United States Patent [19]

Jonas et al.

[11] Patent Number: 4,478,751

[45] Date of Patent: Oct. 23, 1984

[54] COMPLEX SALTS HAVING HIGH ELECTRIC CONDUCTIVITY

[75] Inventors: Friedrich Jonas, Aachen; Jürgen Hocker, Berg.-Gladbach, both of Fed. Rep. of Germany; Bruno Broich, Baden, Switzerland

[73] Assignee: Bayer Aktiengesellschaft, Leverkusen, Fed. Rep. of Germany

[21] Appl. No.: 408,668

[22] Filed: Aug. 16, 1982

[30] Foreign Application Priority Data

Aug. 26, 1981 [DE] Fed. Rep. of Germany ....... 3133738

[51] Int. Cl.$^3$ .............................................. C07C 50/00
[52] U.S. Cl. ................................ 260/396 N; 252/500
[58] Field of Search .................................... 260/396 N

[56] References Cited

U.S. PATENT DOCUMENTS 3,162,641 12/1964 Acker et al. ...................... 260/286

OTHER PUBLICATIONS

Wheland et al., J. Am. Chem. Soc., vol. 98, 3916–3925 (1976).
Chemical Abstracts, vol. 95, No. 10, p. 11, No. 81678p, (Sep. 7, 1981).

*Primary Examiner*—Dolph H. Torrence
*Attorney, Agent, or Firm*—Connolly and Hutz

[57] ABSTRACT

Complex salts of 7,7,8,8-tetracyano-p-quinodimethane having high electric conductivity, process for the preparation thereof and the use thereof as electric conductors, semiconductors or photoconductors and for antistatic finishing of plastics products.

3 Claims, No Drawings

COMPLEX SALTS HAVING HIGH ELECTRIC CONDUCTIVITY

Complex salts of the 7,7,8,8-tetracyano-p-quinodimethane anion (TCNQ)$^\ominus$ corresponding to the following formula:

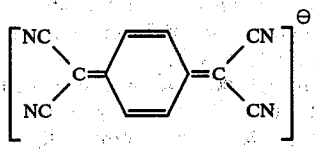

and inorganic or organic cations (e.g. organic ammonium ions) are known to be electrically conductive compounds (see U.S. Pat. No. 3,162,641; J. Am. Chem. Soc. 98 3916 (1976)). Such complexes generally have the following constitution:

wherein
M$^\oplus$ represents an inorganic or organic cation, e.g. a quaternary ammonium ion, phosphonium ion or triaryl sulphonium ion;
TCNQ$^\ominus$ represents a 7,7,8,8-tetracyanoquinodimethane anion; and
n TCNQ represents n neural TCNQ molecules, wherein n represents 0 or an integer of from 1 to 4. For obtaining high electric conductivities in most cases n is ≧1.

Such complexes may be prepared by the reaction of TCNQ with organic cation iodides, e.g. as follows:

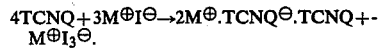

In this reaction, a TCNQ molecule is reduced to the TNCQ$^\ominus$ anion by iodide with liberation of iodine without the iodine being incorporated into the comlex.

It has now surprisingly been found that sulphonium salts may be reacted with TCNQ in suitable organic solvents to form complex salts containing halogen.

The present invention relates to new, electrically conductive TCNQ complexes corresponding to the following general formula (I):

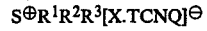

wherein:
R$^1$, R$^2$ and R$^3$ represent identical or different straight- or branched-chain alkyl groups preferably having from 1 to 12 carbon atoms, most preferably from 1 to 6 carbon atoms, or substituted or unsubstituted cycloalkyl groups having preferably from 5 to 12 ring carbon atoms, most preferably from 5 to 7 ring carbon atoms, or substituted or unsubstituted aralkyl groups having preferably from 7 to 12 carbon atoms, most preferably from 7 to 9 atoms;
X represents halogen, preferably iodine; and
TCNQ represents 7,7,8,8-tetracyanoquinodimethane.

The compounds corresponding to general formula (I) may be prepared by reacting tetracyanoquinodimethane and a tertiary sulphonium salt corresponding to the following general formula (II):

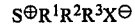

wherein
R$^1$, R$^2$, R$^3$ and X are as defined above in connection with general formula (I);
in a suitable organic solvent at temperatures of from 0° to 120° C., preferably from 20° to 80° C. The TCNQ and sulphonium salt are preferably used in equimolar quantities although a sub-equivalent amount or excess of sulphonium salt may be used.

The organic solvents used may be acetonitrile, acetone or mixtures of acetonitrile and methanol, acetonitrile being preferred. The reaction time may be from 30 minutes to several days and is preferably from 1 to 12 hours. The products are obtained in solid form and may be isolated from the solution by simple filtration.

Particularly suitable sulphonium salts include trimethyl sulphonium iodide, triethylsulphonium iodide, trimethyl sulphonium bromide, triethyl sulphonium bromide, tripropyl sulphonium bromide and iodide, tributyl sulphonium bromide and iodide and dimethyl ethyl sulphonium bromide and iodide, cyclohexylmethyl sulphonium iodide, dicyclohexylmethyl sulphonium iodide, benzyldimethyl sulphonium iodide, tribenzyl sulphonium iodide, tribenzyl sulphonium bromide.

The TCNQ complexes according to the present invention corresponding to general formula (I) have high electric conductivities and may be used as electric conductors, semiconductors and photoconductors.

The compounds may also be incorporated in polymer products, e.g. polycarbonates, to serve as antistatic finishes.

EXAMPLES

Example 1

A solution of 5.3 g of trimethylsulphonium iodide in 250 ml of acetonitrile and 15 ml of ethanol prepared at 60° C. is added to a boiling solution of 4.2 g of TCNQ in 400 ml of acetonitrile. The reaction mixture is cooled slowly and left to stand at room temperature for 12 hours. The solution obtained is then concentrated to a small volume by evaporation, methylene chloride is added and the crystals (II) which precipitate are separated by suction filtration. 8.3 g ($\triangleq$98% of the theoretical yield) of dark green, shiny crystals are obtained, which have an electric conductivity of $2.22 \cdot 10^{-2} \Omega^{-1} cm^{-1}$.

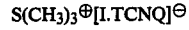

Example 2

2.1 g of TCNQ and 2.1 g of trimethylsulphonium iodide are heated under reflux in 300 ml of acetonitrile (10 minutes). The reaction mixture is then cooled and concentrated by evaporation. The precipitated crystals are suction filtered and dried. 2.9 g (69% of the theoretical yield) of dark green crystals having the constitution S(CH$_3$)$_3$$^\oplus$[I.TCNQ]$^\ominus$ are obtained.

C$_{15}$H$_{13}$IN$_4$S Calc. 44.2% C, 3.2% H, 13.7% N, 31.1% I. Observed 44.8% C, 3.2% H, 14.1% N, 30.1% I.

Example 3

2.1 g of TCNQ and 2.2 g of dimethyl-ethylsulphonium iodide are heated under reflux in 300 ml of acetonitrile (10 minutes). The reaction mixture is then cooled and the precipitated product is suction filtered. 3.2 g (74% of the theoretical yield) of dark green crystals having the constitution $S(CH_3)_2C_2H_5^{\oplus}[I.TCNQ]^{\ominus}$ are obtained.

Example 4

2.1 g of TCNQ and 1.6 g of trimethylsulphonium bromide are reacted as described in Example 3. 1.8 g (49% of the theoretical yield) of dark green crystals having the constitution $S(CH_3)_3^{\oplus}[Br.TCNQ]^{\ominus}$ are obtained.

We claim:

1. A complex corresponding to the following general formula (I):

$$S^{\oplus}R^1R^2R^3[X.TCNQ]^{\ominus} \qquad (I)$$

wherein
$R^1$, $R^2$ and $R^3$ independently represent alkyl, optionally substituted cycloalkyl or optionally substituted aralkyl;
X represents halogen; and
TCNQ represents 7,7,8,8-tetracyano-p-quinodimethane.

2. A process for the preparation of a complex as claimed in claim 1 which comprises reacting a tertiary sulphonium halide corresponding to the following general formula (II):

$$S^{\oplus}R^1R^2R^3X^{\ominus} \qquad (II)$$

wherein
$R^1$, $R^2$, $R^3$ and X are as defined in claim 1;
with 7,7,8,8-tetracyano-p-quinodimethane in an organic solvent at a temperature of from 0° to 120° C.

3. A process as claimed in claim 2 in which the tertiary sulphonium halide is selected from trimethyl sulphonium iodide and bromide, triethyl sulphonium iodide and bromide, tripropyl sulphonium bromide and iodide, tributyl sulphonium bromide and iodide and dimethyl ethyl sulphonium bromide and iodide, cyclohexyldimethyl sulphonium iodide, dicyclohexylmethyl sulphonium iodide, benzyldimethyl sulphonium iodide, tribenzyl sulphonium iodide, tribenzyl sulphonium bromide.

* * * * *